(12) United States Patent
Lipinski et al.

(10) Patent No.: US 9,255,251 B2
(45) Date of Patent: Feb. 9, 2016

(54) PURIFIED BACTERIOPHAGE, ITS PREPARATION AND APPLICATION

(75) Inventors: Tomasz Lipinski, Wroclaw (PL); Andrzej Gamian, Wroclaw (PL); Ewa Zuziak, Brzeg Dolny (PL); Agnieszka Korzeniowska-Kowal, Miekinia (PL); Andrzej Gorski, Wroclaw (PL)

(73) Assignee: Instytut Immunologii i Terapii Doswiadczalnej Pan, Wroclaw (PL)

( * ) Notice: Subject to any disclaimer, the term of this patent is extended or adjusted under 35 U.S.C. 154(b) by 883 days.

(21) Appl. No.: 12/449,418

(22) PCT Filed: Feb. 8, 2008

(86) PCT No.: PCT/PL2008/000013
§ 371 (c)(1),
(2), (4) Date: May 25, 2010

(87) PCT Pub. No.: WO2008/097115
PCT Pub. Date: Aug. 14, 2008

(65) Prior Publication Data
US 2011/0008873 A1   Jan. 13, 2011

(30) Foreign Application Priority Data
Feb. 9, 2007  (PL) .......................................... 381730

(51) Int. Cl.
*C12N 7/00*  (2006.01)
*C12N 7/02*  (2006.01)
*A61K 35/76*  (2015.01)

(52) U.S. Cl.
CPC . *C12N 7/00* (2013.01); *A61K 35/76* (2013.01); *C12N 7/02* (2013.01); *C12N 2795/00011* (2013.01); *C12N 2795/00051* (2013.01); *C12N 2795/10132* (2013.01); *C12N 2795/10151* (2013.01)

(58) Field of Classification Search
None
See application file for complete search history.

(56) References Cited

U.S. PATENT DOCUMENTS 5,589,591 A * 12/1996 Lewis ........................... 536/128

FOREIGN PATENT DOCUMENTS

CA   2304123   10/2001
GB   2327945   2/1999

OTHER PUBLICATIONS

Jarrell et al., Journal of Virology, 1981, 38(2):529-538.*
Brown et al., J Bacteriol., 1962, 83(3): 697-698.*
Dean et al., Biotechnology Techniques, 1992, 6(2):133-138.*
Mathes et al., Journal of Clinical Microbiology, 1977, 5(3):372-374.*
Paul et al., Applied and Environmental Microbiology, 1991, 57(8):2197-2204.*
Rybka et al., Journal of Microbiological Methods, 2006, 64:171-184.*
Schade et al., Overly Biochemical Research Foundation, 1944, 179-190.*
An et al., Int. J. Mol. Sci., 2013, 14:3556-3567.*
Kanayama et al., Biol. Pharm. Bull., 2007, 30(2):237-241.*
Zuziak et al., 2nd Baltic Meeting on Microbial Carbohydrates, Oct. 2006, p. 42.*
International Search Report issued by the International Searching Authority (ISA/EP) on Nov. 11, 2008 in connection with International Application No. PCT/PL2008/000013.
WO 2004/003184 A1 (Inst Immunologii I Terapii Dos) Jan. 8, 2004.
WO 2005/024005 A1 (Intralytix Inc) Mar. 17, 2005.
Boratynski, Janusz et al., "Preparation of endotoxin-free bacteriophages", Cellular & Molecular Biology Letters, vol. 9, No. 2, (2004), pp. 253-259.
Jul. 15, 2014 Communication, issued in connection with European Patent Application No. 08712679.3.
Nov. 20, 2014 Response, filed in connection with European Patent Application No. 08712679.3.
Dec. 16, 2014 Communication, issued in connection with European Patent Application No. 08712679.3.
Russel and Model (1989) Genetic Analysis of the Filamentous Bacteriophage Packaging Signal and of the Proteins That Interact with It. Journal of Virology, 3284-95.
Dybvig et al. (1985) Identification of an Enveloped Phage, Mycoplasma Virus L172, that Contains a 14-Kilobase Single-Stranded DNA Genome. Journal of Virology, 384-90.

* cited by examiner

*Primary Examiner* — Nicole Kinsey White
(74) *Attorney, Agent, or Firm* — Gary J. Gershik; Cooper & Dunham LLP

(57) ABSTRACT

A method of preparation of purified bacteriophage with increased antibacterial activity, in which from bacterial lysate of phages is obtained, advantageously in the presence of lysozyme, chelating factor and detergent, in a continuous manner with ultrafiltration on membranes, the phage containing high molecular mass preparation, devoid of bacterial cell wall and other contaminants, free of toxins and endotoxins, active in tests of bacterial lysis, which is characterized by chromatography HPLC, In SDS-PAGE electrophoresis, immunoblotting, biological tests of bacterial lysis, and is dedicated for phage therapy of bacterial infections and tumors and for production of phage deriving pharmaceutical preparations.

9 Claims, No Drawings

PURIFIED BACTERIOPHAGE, ITS PREPARATION AND APPLICATION

This application is a §371 national stage of PCT International Application No. PCT/PL2008/000013, filed Feb. 8, 2008, and claims priority of Polish Patent Application No. P.381730, filed Feb. 9, 2007, the contents of all of which are hereby incorporated by reference into this application.

The invention concerns a method of bacteriophage purification which permits to retain high antibacterial activity of phage particles dedicated to phage therapy of bacterial infections and cancer diseases and also production of phage derived pharmaceutical preparations.

Bacteriophages being viruses infecting bacteria, are a natural factor controlling the quantity of bacterial population in nature. The observed increasing number of pathogenic bacteria resistant to currently used antibiotics, requires the exploration of alternative antibacterial therapies [i]. Because of their nature bacteriophages seem to be ideal candidates for modern effective antibacterial tool. The growth of interest in phage or phage proteins as therapeutic tools is related to the reported by some research centers the healing effectiveness by bacteriophages in cases where antibiotic appeared to be not effective [ii, iii]. Bacteriophages are complexes of several proteins and nucleic acid, DNA or RNA. The nucleic acid can be in a form of single or double stranded closed loop or filament closed in protein capsule. The phage proteins can self arrange into morphological forms allowing to distinguish a head, tail, adhesion plate and phage fibers [iv, v]. Some of the proteins express an enzymatic activity which is necessary for destroying of bacterial wall or bacterial envelope. Therefore some purified phage proteins can be potentially very important antibacterial factors[vi] or they can be valuable commercial enzymes. Bacteriophages may have a lytic cycle or a lysogenic cycle, but a few viruses are capable of carrying out both. With lytic phages, bacterial cells are broken (lysed) and destroyed after immediate replication of the virion. As soon as the cell is destroyed, the new bacteriophages viruses can find new hosts. Infection of liquid bacterial culture by bacteriophage can make its complete sterile. In contrast, the lysogenic cycle does not result in immediate lysis of the host cell. Those phages able to undergo lysogeny are known as temperate phages and they are not suitable for phage therapy.

Probably one phage can infect only one bacterial strain, but polyvalent bacteriophages infecting wide group of bacterial are more interesting. If we get knowledge about techniques of bacteriophage treatment we can have a very inexpensive and unlimited source of new effective antibiotics. As we know making a classic chemical antibiotic is due to high cost. Moreover, bacteriophages are specific and they don't infect all of bacteria present in our organism. Symbiotic bacteria can exist and the micro flora is intact. The conventional antibiotics are not selective and sterilize human organism which cause a lot of complications such as mycosis. Bacteriophages demonstrate a lot of advantages [vii]. The concentration of phage particles in physiological fluids of sick person is stable after application and can undergo self-control. The number of phage particles exponentially grows in a presence and decrease in the absent of bacteria. There are no side effects during phage therapy. Selected phages can be used in protective purposes such as sanitization for example wards. Bacteria are rarer resistant to phages than to antibiotics. Moreover, if bacteria becomes resistant to the phage, there is another one which can infect this bacterium. Bacteriophages can be also use with antibiotics in combined therapy. If we want to apply bacteriophage therapy, we should have a method to obtain bacteriophages without bacterial contaminants and with high activity.

Filtration step is a part of bacteriophage purification in laboratory scale. In U.S. Pat. No. 6,121,036 a membrane filtration was described with cut off from 0.01 to 1 μm advantageously from 0.1 to 0.5 μm, the most preferably from 0.2 to 0.4 μm which allow to keep bacteria but not bacteriophages. In order to remove from filtrate of endotoxins and toxins contaminants, the bacteriophage preparation was ultracentrifuged, dialyzed, gel filtrated and ultrafiltrated. The description involved parameters used in applied techniques, regarding ultrafiltration the bacteriophage preparation is filtered on a membrane with cut off from $10^4$ to $10^7$ Da, preferentially from $10^5$ to $10^6$ Da. According to this method the bacteriophage preparations obtained were specific to selected bacteria, virulent and effective in vivo and purified with endotoxin level less than 1% of endotoxin weight, advantageously lower than 0.05% weight endotoxins. Phages purification and endotoxins removing was done by cycle of centrifugation, filtration and molecular filtration technique.

In U.S. Pat. No. 6,485,902 to obtain bacteriophage particles used then in veterinary therapy against *E. coli*, the biological material was filtered on 0.22 μm filter.

In patent application No WO 2004/091505 authors revealed the usage of lytic bacteriophage against *Methylobacterium* which was purified by filtration of supernatant on 0.22 μm filter, retaining bacterial cells but not bacteriophage particles. The obtained bacteriophage preparation was ultrafiltrated using membrane with cut off from $10^4$ to $10^7$ Da, advantageously from $10^5$ to $10^6$ daltons.

The isolation procedure described in patent application WO 2006/050193 was based on filtration and then concentration of bacteriophage particles. The MILLIPORE filters were used with cut offs which were sufficient to keep bacteriophage but not bacterial cells, near 0.45 to 0.22 μm.

In other known methods the bacteriophage particles were purified by ammonium sulphate precipitation, dialysis, or polyethylene glycol precipitation [viii, ix] and also by ultracentrifugation using cesium chloride, or saccharose gradient [viii, ix, x, xi]. In other methods polysaccharide or other esters were used [xii] or polyanionic membrane [xiii] or combined multi steps procedures with polyethylene glycol precipitation and polyanionic membrane filtration and molecular filtration on chromatographic columns [xiv]. Despite multiple purifications the results are not repetitive. There is no chance to get a specimen with identical activity and identical purification level. Serious disadvantage of these methods is a multiple steps purification process of purification which causes decrease of activity and purification yield of bacteriophages so there is a necessity of efficient manner of bacteriophage purification which could be use in industrial scale.

The subject of this invention is the procedure of bacteriophage purification and its relevance relies on that;

a) The bacteriophage lysate is obtained by growing the host bacteria in a liquid culture medium, and then b) The purification and concentration is made in a continuous manner using selective permeable membrane which retains bacteriophages but not low molecular molecules, c) Incubation of concentrated bacteriophages with at least one of the factor, namely containing enzymes, chelating agents, detergents or washing buffers.

d) Purification and concentration of lysate obtained in b) is continued in continuous manner using selective permeable membrane which retains bacteriophages but not low molecular mass molecules, but the bacteriophage particles can return again to b)

e) Concentration of preparation obtained in c) and d) and finally the purified bacteriophage is obtained.

Advantageously the method in this invention is characterized by that a) in liquid medium, advantageously based on casein hydrolysate, lysate with phages is obtained in bioreactor, advantageously with controlled aeration and magnetic stirring.

Advantageously the method in this invention is characterized by that in b) the preparation with phages, advantageously is rinsed with phosphate buffer, and very gentle concentrated by ultrafiltration with circulation of purified material.

Advantageously the method in this invention is characterized by that in c) the fraction with phages is treated with detergent advantageously with 0.5-2% sodium deoxycholate in order to endotoxin removal.

Advantageously the method in this invention is characterized by that in b) the selective membrane is used with cut off 1000 kDa in order to removal of molecules under 1000 kDa.

Advantageously the method in this invention is characterized by that in c) the fraction with phages is rinsed with chelating agent, advantageously EDTA and digested by lyzozyme.

Advantageously the method in this invention is characterized by that in d) the selective membrane is used with cut off 100 kDa molecules in order to their removal.

Advantageously the method in this invention is characterized by that in additionally obtained in e) preparation is comprehensively analyzed to indicate a presence of bacterial wall elements, endotoxins by LAL and Kdo, HPLC chromatography, SDS-PAGE; immunoblotting with human sera, biological tests on bacterial lysis and comparing with other bacteriophages specimens obtained using other methods of purification.

The subject of the invention is also the bacteriophage preparation of increased antibacterial activity obtained using this method, basically devoid of bacterial wall and other contaminants such as bacterial proteins and lipids especially endotoxins and toxins.

The crucial parameter which is used for purity level determination is calculation of the endotoxin concentration. It is worth to say that decrease of endotoxin level in bacteriophage specimen using this method of purification is also a measure of decreasing of other bacterial contaminants such as proteins or lipids. Advantageously the level of endotoxin in bacteriophage specimen obtained by this method is less than 1 unit of endotoxin EU/mg of weight amount of bacteriophage specimen advantageously less than 0.05 EU/mg when the endotoxin level is measured by LAL and Kdo tests.

The parameter which is used to determine the activity of obtained phages is phage titer. Advantageously the level of the specimen obtained by this method is $10^7$ pfu/ml, advantageously more than $10^8$ pfu/ml the most favorably more than $10^9$ pfu/ml. Titer of phage can be calculated by methods described below in examples.

The next subject of the invention is using of obtained bacteriophage specimens to produce pharmaceuticals.

Advantageously the pharmaceutical phage is used in phage therapy more advantageously in treatment or prevention bacterial infections or tumors.

The invention is devoid of drawbacks known in other methods, because of 1) reduction of steps and constant flow and 2) elimination of drastic stages and making the procedure milder. Bacteriophage specimens can be used for phage therapy, production of derivatives for biological and immunological investigations, including reactivity with phages, nevertheless if the phages are not sufficiently purified the cross reactivity can occur or other unwanted reactions with bacterial agents (endo- and exotoxins, bacterial proteins, polysaccharides, lipids, LPS and other). There are antibodies against these elements in human sera, so to obtain save medicaments and reliable data there is necessity to precise and repetitive bacteriophage purification. Very important is improvement of known bacteriophage production methods, which thanks to this solution proposed in this application, allows the using phage in therapy in practice.

This invention is based on the study of three E. coli phages, namely K1 phage—laboratory phage—for tests elaboration, I11m phage most common in recent experimental therapy, and multivalent phage—T4 which can infect many E. coli. species. These bacteria can cause a lot of diseases. Novelty of this invention concerns original solutions in bacteriophages production and purification and also using modern methods of analysis of the bacteriophage purity level, These are: chromatography methods, SDS-PAGE, LAL test for endotoxin level measurement and chemical method GLC-MS (method Kdo [xv]). So far there was no sufficient sensitive method for bacteriophage purity measurement. Innovate solution in this invention is constant bacteriophage purification using filtration and concentration on Pellicon system with membrane with cut off 1000 kDa and 100 kDa with using detergent, advantageously sodium deoxycholate and chelating agent and lysozyme. Finally the specimen was concentrated by ultrafiltration on Amicon. Filtration step was designed in such a way that low molecular weight molecules flow through the membrane without phage particles. The bacteriophage particles leave the chamber and return to it in closed circuit and circulate becoming more concentrated. The first module is connected with another one which contains a new membrane. Using connected in-line two modules advantageously with two different membrane cut offs provides continuity of process with homogeneous material flows and continuous circulation. In the circulation the chamber with detergent, enzyme and buffers were added before membrane stage. The phage titration was done by Grattie or RTD method, and the protein concentration was calculated using Lowry test. The bacteriophage specimens were subjected to SDS-PAGE and preparative electrophoresis to prepare bacteriophage proteins. After electrophoresis gels were incubated with Coomasie Brilliant Blue or were stained with silver and analyzed in immunoblotting test with human sera. Using lysozyme and chelating agent at the same time allowed for more effective degradation of bacterial wall because chelating agent can destabilize cell membrane and facilitate the lysozyme access to its substrate. Thanks to the circulating with constant flow filtration and concentration system the bacterial digestion products were filtered out and didn't interrupt in the next stages of bacteriophage purification. Using detergent with chelating agent was fundamental element of the invention, because it allowed removing bacterial hydrophobic molecules such as membrane proteins and lipids without phage particles destroying. Unexpectedly the agents caused increase of bacteriophage activity in the same volume, probably because they can liberate from bacterial contaminants. This invention describes also the methodology of purity analysis of purified phages and their characterization with reactivity with human sera. The complex analysis of phage preparation purity (example 5) is due to tests for the presence of bacterial wall components, endotoxin presence with LAL and Kdo tests, HPLC chromatography, electrophoresis in the presence of SDS, immunoblotting with human sera, biological tests of bacterial lysis (example 4), comparing with specimens obtained using other methods (example 3). It should be emphasized that phage therapy is very effective, not only in Institute of Immunology and Experimental Therapy in Wroclaw, but also in other centers in the World [xvi, xvii, xviii, xix]. Implementation of phage specimens' production in large industrial scale as inexpensive could be better for pharmaceutical industries. This could be good alternative for antibiotics which very often become ineffective. Effective analytical methods for phage purity determination which are proposed in this invention, can be used as a subject of purity bacteriophage specimens' specification. Phage specimens obtained by methods described in this innovation can be used in phage therapy, or anticancer and infections treatment and also as a pharmaceutical basis.

The procedure of bacteriophage production was elaborated advantageously on casein hydrolysate, then purified, which allowed obtaining bacteriophage on large scale and with high titer of activity. Previously contaminants of phages such as bacterial endotoxins didn't allow for their use in a wide range of applications. Obtaining a big mass of phage particles allows separating their protein components.

EXAMPLES

1. Bacteriophage Growing on Bacterial Culture

*E. coli* B, and T4 phage were from Polish Collection of Microorganisms located in Institute of Immunology and Experimental Therapy, Polish Academy of Sciences in Wroclaw. The test-tubes with 5 ml of LB were inoculated by *E. coli* B from agar plate. The inoculum was incubated overnight at 37° C., next were moved into 100 ml of LB with 0.5% glucose (1 ml of 50% glucose was added). Bacterial growth was controlled by absorption measurement at 600 nm against LB. Bacterial culture was carrying about 3-4 hours to reach $A_{600}=1.0$ which means $10^9$ cfu/ml of bacteria titer. Then bacteria were centrifuged at 5000×g, 15 min, 4° C., (Heraeus) in falcons (Sarstedt, 45 ml). Bacterial cells were removed to 20 ml of LB and next to bacteriophage medium LB or casein hydrolysate with 1.2 ml 2.5 M $MgCl_2$ (the final concentration of 2.5 mM) and 12 ml 50% glucose (to the final concentration of 0.5%). The phage culture was carrying in 2 l bottle with aeration on magnetic mixer at 37° C. to reach A 600=1.0. Next step was bacteriophage particles adding (80 ml of T4 phage 1.4×$10^{10}$ pfu/ml titration). The ratio of bacteriophage to bacteria should be about 1:1, more advantageously when there is more phage particles than bacterial cells. 5 minutes after infection by phage the glucose was added 12 ml 50% of glucose (to the final concentration of 0.5%), and 30 minutes after infection indol was added 300 ml 5 mM of indol (to the final concentration of 1 mM). Lyses of bacterial cells were carrying with aeration on magnetic mixer at 37° C. and the A 600 nm was controlled during lyses (about 4 h). After that chloroform was added to the final concentration of 1%. Then it was cooled in water bath to reach 4° C. and centrifuged (5000×g, 15 min, 5° C., Heraeus). The supernatant with phage was filtered throw antibacterial filter of 0.22 μm. The filtration was in sterile box using STERITOP filter by Millipore. The phage specimen was stored at 4° C. Phage titration is made using Grattie or RTD (Routine Test Dilution) method. The phage activity is assigned as pfu/ml (plaque-forming units). The phage production capacity is the ratio of phage particles level obtained by this method, described above, to phage particles level obtained by other general using methods.

2. Phage Purification from Bacterial Lysate

After phage production the specimen is filtered throw 1000 kDa membrane (PLCXK, Millipore) using mini holder Pellikon (Millipore). After that the phage culture is 5 times concentrated and partially purified. Filtration step was designed that low molecular weight molecules flow through the membrane without phage particles. The bacteriophage particles leave the chamber and return to it in closed circuit and circulate becoming more concentrated. The first module is connected with another one which contains a new membrane. The pressure is always controlled on input and output of the chamber. This is the first module which is connected with another one by hoses. The second module has a 100 kDa membrane (PLCHK, Millipore) also on mini holder. Using connected in-line two modules advantageously with two different membrane cut offs provides continuity of process with homogeneous material flows and continuous circulation. In the circulation the chamber with detergent, enzyme and buffers were added before membrane stage. To the bacteriophage specimen detergent was added, advantageously DOC, to the final concentration of 1%, and after overnight at 4° C. the specimen was again filtered using 100 kDa membrane and washed with buffer—0.05 M Tris/HCl pH 8.0 with 0.25 M NaCl and with 0.005 M $MgCl_2$, and next the specimen was washed with phosphate buffer 0.05 M pH 7, with 5 mM EDTA (0.05 M $Na_2HPO_4$ and 0.05 M $NaH_2PO_4$ were mixed in the ratio to allowed to reach the final pH of 7.0), and after lysozyme treatment (38500 U/mg, Sigma) to the final concentration of 0.05% the bacterial murein was overnight digested at. 4° C. The 100 kDa membrane filtration was continued till the lysozyme was removed, advantageously to reach A 208<0.05 AU (Absorption Units). At the end the specimen was concentrated using AMICON ultrafiltration and membrane with cut off 100 kDa (PLHK, Millipore). Most often the 100 ml of phage specimen was obtained, it was 200 times concentrated (20 l to 100 ml) with simultaneous purification of phage, without bacterial endotoxin measured in LAL test, for example T4 phage 2.9×$10^4$ EU/ml and I11m phage 1.2×$10^3$ EU/ml. Endotoxin reduction can be obtained by repeated cycles of filtration. The phage purification capacity was for example 10% in a case of T4 or 17% in a case of I11m (7×$10^9$ pfu/ml the starting trite 2×$10^{10}$ pfu/ml). According to the invention the phage specimens were obtained with endotoxin level of less than 1 unit of endotoxin EU/mg of weight amount of bacteriophage specimen advantageously less than 0.05 EU/mg, the 1 ng is 5 EU (endotoxin units). The phage purification capacity was almost the same as the other purified by cesium chloride ultracentrifugation method and was 10-30% of initial culture activity.

3. Purification Phage by Polyethylene Glycol Precipitation and Ultracentrifugation Method After T4 phage culture polyethylene glycol was added (PEG) 6000 Da (to the final concentration of 8%) with 0.5 M NaCl and mixed for 15 minutes at 37° C., for PEG to be dissolved. Next the specimen was incubated about 24 h at 4° C., then ultracentrifugated (17000 rpm, 3 h, 4° C., Heraeus), and supernatant was removed and the pellet was dissolved in 20 ml of T-phage buffer. In the next step KCl was added (to the final concentration of 1 M) mixed very gently for 15 minutes. The specimen was ultracentrifuged (10000 rpm, 20 min, 4° C.), and CsCl was added to the supernatant (to the final concentration of 0.01 M). Ultracentrifuged in special tubes (32000 rpm for 24 h, 4° C., Beckman). The obtained fraction was dialyzed to the 0.1 M Tris/HCl buffer, pH 8.0, with NaCl 0.5 M, $MgCl_2$ 0.01 M.

To purify the phage the saccharose gradient was made in special tubes using saccharose dilutions: 32.25%, 22.5%, 13.75% and 5%. All of the dilutions were placed in ultracentrifuge tubes (Beckman) in turn: 4 ml of 40%, 4 ml of 32.25%, 4 ml of 22.5%, 4 ml of 13.75% and 4 ml of 4% of saccharose. The tubes were incubated overnight at 4° C. and the saccharose linear gradient was made. After that the phage specimen was applied on the surface of the saccharose gradient. The tubes were balanced and centrifuged (50000 rpm, 5 h, 4° C., Beckman). After ultracentrifugation the tubes were put on ice and the specimen was fractionated taking 0.5 ml of the specimen. The fractions were overnight dialyzed to the mili Q water and analyzed in SDS-PAGE electrophoresis.

4. Phage Titration

Phage titration is made by Grattie or RTD (Routine Test Dilution) methods as phage particles value infecting bacteria in 1 ml. The unit of titrate is pfu/ml [plague-forming units/mil]. Tubes with 5 ml of LB were inoculated by *E. coli* B cells from agar plate culture. The inoculum was incubated at 37° C. for 3 h. The decimal dilutions of phage were made in PBS. In sterile tubes the liquid 0.7% agar (3 ml) was prepared each of tube was held on 80° C. in water bath. Plates with phage medium (NaCl 5.0 g, $Na_2HPO_4$ 3.0 g, agar 17.0 g, casein hydrolyzate 10.0 g, meet extract 3.0 g), were dried under UV lamp. Liquid agar was cooled to temperature about. 40° C., and next the 0.2 ml of bacterial strains was added and 0.2 ml of phage solution (each solution) mixed and put on plate, one tube per one phage plate. After drying the plates were overnight incubated at 37° C.

The RTD Method.

Tubes with 5 ml of LB inoculated by *E. coli* B cells from agar plate culture. The inoculum was incubated at 37° C. for 3 h. The decimal dilutions of phage were made in PBS Plates with phage medium were drying under UV lamp. Next the bacterial culture was put on it (2 ml of *E. coli* B) and leaved to dry, about for 15 minutes. After that the 10 μl of phage was put on the plate and the plates were incubated over night at 37° C.

5. Phage Preparations Analysis of Purity

Phage proteins were analyzed in SDS-PAGE electrophoresis by Laemmli method. In electrode buffer pH 8.61 in 10% or 12.5% gels. The specimens before analysis were dried at 37° C. and than they were diluted in mili Q water and buffer (2× concentrated) and boiled for 3 minutes. Electrophoresis lasted for about 1 h, the plates dimensions were 83×73×0.75 mm, and the current was 10 mA, and then 20 mA per plate [BioRad]. The gels were stained by 1% Coomassie Brilliant Blue R-250, for 30 minutes and destained by 40% methanol with 10% acetic acid. The gels were stained also by silver reagent. Gels were incubated overnight in 40% methanol with 10% acetic acid and then on shaker with 0.7% $HIO_4$, for 5 minutes. Next they were washed 4×10 minutes with mili Q water. The gels was incubated with silver reagent for 10 min., washed 4×10 min. with mili Q water and detected.

Immunoblotting was made after electrophoresis using gel incubated in transfer buffer (incubation for 15 minutes). The Immobilon-P membrane washed 15 sec in 100% MeOH, 2 minutes in mili Q water, 2 minutes in transfer buffer. Transfer was lasting for 1 h (100 V of the voltage) [BioRad]. The membrane after transfer was incubated with Ponceau S, and next with milli Q water and dried membrane on Whatman 1 and stored safely. Membrane wet in 100% MeOH and washed mili Q water, and next blocked by 1% BSA in TBS-T buffer (TBS+0.05% Tween 20 with 0.5 ml of 1% BSA) at 37° C. for 1 h. The membrane was washed with TBS-T 1×15 minutes twice 5 minutes. Next the immobilon-P incubated with human sera dilutions (250× diluted) (5 ml TBS-T z 1% BSA+ 20 μl sera). First stage was at 37° C. for 1 h with shaking and the second at 4° C. overnight. Non bound antibodies were removed by washing the membrane with TBS-T (once 15 minutes and 2×5 minutes). The solution was prepared of goat antibodies anti-Human IgG with alkaline phosphatase (0.5 μl of antibodies in 10 ml of TBS-T with 1% BSA) and the membrane was incubated with it at 37° C., for 1 h. Washed with TBS. Detected—5 ml of TBS-$Mg^{2+}$ with 50 μl BCIP (30 mg/ml in 70% DMF) and 50 μl NBT (15 mg/ml in 100% DMF).

[i] Biswas B., Adhya S., Washart P., Brain P., Trostel A. N., Powell B., Carlton R., and Merril C. R. (2002): Bacteriophage therapy rescues mice bacteremic from clinical isolate of vancomycine-resistant *Enterococcus faecium*. Infect. Immun., 204-210

[ii] Sulakvelidze A., Morris J. G. (2001): Bacteriophages as therapeutic agents. Ann Med. 33 (8):507-509

[iii] Kucharewicz-Krukowska A., Ślopek S. (1987): Immunogenic effect of bacteriophage in patients subjected to phage therapy. Arch. Immunol. Ther. Exp. 35: 553-561

[iv] Zaremba M. L., Borowski J.: Mikrobiologia lekarska, Warszawa (1997) Wydawnictwo Lekarskie PZWL

[v] Ross F. C.: Introductory Microbiology, (1983), Merril C. E. Publishing Co., A. Bell and Howell Company

[vi] Loeffler J. M., Nelson D., Fischetti V. A. (2001): Rapid killing of *Streptococcus pneumoniae* with bacteriophage cell wall hydrolase. Science 294 (5549):2170-2172

[vii] Carlton R. M. (1999): Phage therapy: past history and future prospects. Arch. Immunol. Ther. Exp., 47, 267-274

[viii] Ehara M., Shimodori S., Kojima F., Ichinose Y., Hirayama T., Albert M J., Supawat K., Honma Y., Iwanaga M., Amoko K. (1997): Characterisation of filamentous phages of *Vibrio cholerae* O139 and O1. FEMS Microbiol. Let. 154:293-301

[ix] Svenson S B., Lonngren J., Karlin N. and Lindberg A A. (1979): *Salmonella* bacteriophage glucanases: endorhamnosidases of *Salmonella typhimurium* bacteriophages. J. Virol. 1979:583-592

[x] Merril C R., Biswas B., Carlton R., Jensen N C., Creed G J., Zullo S. and Adhya S. (1996): Long-circulating bacteriophage as antibacterial agents. Proc. Natl. Acad. Sci. USA 93:3188-3192

[xi] Nimmich W., Schmidt G., Krallmann-Wenzel U. (1991): Two different *Escherichia coli* capsular polysaccharide depolymerases each associated with one of the coliphage ΦK5 and ΦK20. FEMS Microbiol. Let. 82:137-142

[xii] Boratyński J., Górski A., Syper D., Weber-Dąbrowska B., Polish patent application P.354822

[xiii] Weber-Dąbrowska B., Mulczyk M., Górski A., Boratyński J., Łusiak M., Syper D., Polish patent application P.370662

[xiv] Boratyński J., Górski A., Lipiński T., Syper D., Weber-Dąbrowska B., 2002, Polish patent application P.356897

[xv] Rybka J., Gamian A., Determination of endotoxin by the measurement of the acetylated methyl glycoside derivative of Kdo with gas-liquid chromatography-mass spectrometry, J. Microbiol. Meth., 2006, 64, 171-184.

[xvi] Ślopek S., Durlakowa I., Weber-Dąbrowska B., Kucharewicz-Krukowska A., Dąbrowski M. and Bisikiewicz R. (1981): Results of bacteriophage treatment of suppurative bacterial infections I. General evaluation of the results. Arch. Immunol. Ther. Exp. 31:267-291.

[xvii] Ślopek S., Kucharewicz-Krukowska A., Weber-Dąbrowska B., Dąbrowski M (1985): Results of bacteriophage treatment of suppurative bacterial infections. IV. Evaluation of the results obtained in 370 cases. Arch. Immunol. Ther. Exp. 33 (2):219-40 xviii Ślopek S., Kucharewicz-Krukowska A., Weber-Dąbrowska B., Dąabrowski M. (1985): Results of bacteriophage treatment of suppurative bacterial infections. V. Evaluation of the results obtained in children, Arch. Immunol. Ther. Exp. 33 (2):241-59 xix Ślopek S., Weber-Dąbrowska B., Dąbrowski M. and Kucharewicz-Krukowska A. (1987): Results of bacteriophage treatment of suppurative bacterial infections in the years 1981-1986. Arch. Immunol. Ther. Exp. 35:569-583.

The invention claimed is:

1. A process of preparing a purified and concentrated bacteriophage having an endotoxin level of less than 1 unit per mg of bacteriophage (EU/mg) when measured by both the LAL test and the Kdo test, comprising the following steps:
   a) obtaining a bacterial lysate comprising a bacteriophage;
   b) performing a continuous flow process which circulates the bacterial lysate to purify and concentrate the bacteriophage, the continuous flow process comprising the steps:
      i. contacting the bacterial lysate with a first selective membrane which retains bacteriophage and removes low molecular mass molecules to increase the purity and concentration of bacteriophage to produce concentrated bacteriophage,
         wherein said first selective membrane removes molecules with a molecular mass lower than 1000 kDa,
      ii. passing the concentrated bacteriophage in continuous flow through a chamber, where the concentrated bacteriophage is treated with lysozyme and at least one chelating factor, detergent and washing buffer to produce treated concentrated bacteriophage, and
      iii. contacting the treated concentrated bacteriophage with a second selective membrane which retains bacteriophage and removes low molecular mass molecules to increase the purity and concentration of bacteriophage in the treated concentrated bacteriophage to produce purified and concentrated bacteriophage,
         wherein said second selective membrane removes molecules with a molecular mass lower than 100 kDa; and
   c) obtaining the bacteriophage purified and concentrated in step b), which is concentrated to 200 times its original concentration in the bacterial lysate of step a) and has an activity of more than $10^8$ pfu/ml as determined by phage titer.

2. The process according to claim 1, wherein the bacterial lysate of step a) is obtained from a liquid medium cultured in a fermentor.

3. The process according to claim 1, wherein step b)(i) further comprises washing with phosphate buffer, ultrafiltration, and circulation of bacterial lysate.

4. The process according to claim 1, further comprising step d) after step c), said step d) comprising analyzing the purified and concentrated bacteriophage for the presence of bacterial cell wall components and endotoxin by use of the LAL and Kdo methods.

5. The process according to claim 2, wherein the liquid medium is based on casein hydrolysate.

6. The process according to claim 1, wherein the detergent is 0.5% sodium deoxycholate.

7. The process according to claim 1, wherein the chelating factor is EDTA.

8. The process of claim 1, wherein the purified and concentrated bacteriophage obtained in step (c) has an activity of more than $10^9$ pfu/ml as determined by phage titer.

9. The process of claim 8, wherein the bacteriophage obtained in step (c) has an endotoxin level of less than 0.05 EU/mg when measured by both the LAL test and the Kdo test.

* * * * *